US006034053A

United States Patent [19]
Uckun et al.

[11] Patent Number: 6,034,053
[45] Date of Patent: Mar. 7, 2000

[54] EGF-ISOFLAVONE CONJUGATES FOR THE PREVENTION OF RESTENOSIS

[75] Inventors: Fatih M. Uckun, White Bear Lake; Vuong N. Trieu, Roseville, both of Minn.

[73] Assignee: Wayne Hughes Institute, Roseville, Minn.

[21] Appl. No.: 09/114,680

[22] Filed: Jul. 13, 1998

[51] Int. Cl.[7] .......................... A61K 39/385; A61K 38/25
[52] U.S. Cl. ............................ 514/2; 514/2; 424/195.11; 424/185.1; 424/192.1; 424/193.1; 424/194.1; 530/391.7
[58] Field of Search ................... 514/24, 12, 2; 424/195.11, 192.1, 185.1, 193.7, 193.3, 193.5

[56] References Cited

U.S. PATENT DOCUMENTS

| | | | |
|---|---|---|---|
| 5,587,459 | 12/1996 | Uckun | 530/391.1 |
| 5,911,995 | 6/1999 | Uckun | 424/195.11 |

OTHER PUBLICATIONS

Aikyama, T., et al., 1987, *J. Biol. Chem.* 262, 5592–5595 "Genistein, a Specific Inhibitor of Tyrosine–Specific Protein Kinases".

Banks, J. G., et al., 1985, *J. Appl. Bacteriol.* 58, 391–400 "The Cytotoxic and Photodynamic Inactivation of Microorganisms by Rose Bengal".

Broome, M. A. et al., 1996, *J. Biol. Chem.* 271, 16798–16806 "Requirement for c–Src Catalytic Activity and the SH3 Domain in Platelet—Derived Growth Factor BB and Epidermal Growth Factor Mitogenic Signaling".

Earp, H. S., et al., 1995, *Breast Cancer Research & Treatment* 35, 115–132 "Heterodimerization and Functional Interaction Between EGF Receptor Family Members: a New Signaling Paradigm with Implications for Breast Cancer Research".

Fox, S.B., 1994, *Breast Cancer Research & Treatment* 29, 41–49 "The Epidermal Growth Factor Receptor as a Prognostic Marker; Results of 370 Patients and Review of 3009 Patients".

Landzberg, B.R., et al., 1997, *Prog. Cardiovascular Diseases* 39, 361–298 "Pathophysiology and Pharmacological Approaches for Prevention of Coronary Artery Restenosis Following Coronary Artery Balloon Angioplasty and Related Procedures".

Mullins, D.E., et al., 1994, *Arterioscler. Thromb.* 14, 1047–1055 "Inhibition of PDGF Receptor Binding and PDGF—Stimulated Biological Activity in vitro and of Intimal Lesion Formation in vivo by 2—Bromomethyl—5—Chlorobenzene Sulfonylphthalimide".

Muthuswamy, S.K., 1994, *Molecular & Cellular Biology 14*, 735–743 "Mammary Tumors Expressing the Neu Proto—Oncogene Possess Elevated $c^{Src}$ Tyrosine Kinase Activity".

Ottenhoff–Kalff, A.K., et al., 1992, *Cancer Research* 52, 4773–4778 "Characterization of Protein Tyrosine Kinases from Human Breast Cancer: Involvement of the $c^{Src}$ Oncogen Product".

Saltis, J., et al., 1995, *Atherosclerosis* 118, 77–87 "Expression of Growth Factor Receptors in Arterial Smooth Muscle Cells. Dependency on Cell Phenotype and Serum Factors".

Uckun, F.M., et al., 1995, *Science* 267, 886–891 "Biotherapy of B–13 cell Precursor Leukemia by Targeting Genistein to CD19–Associated Tyrosine Kinases".

Uckun, F.M., et al., 1998, *Clinical Cancer Research*, 4:901–912 "Cytotoxic Activity of EGF—Genistein Against Human Breast Cancer Cells".

Uckun, F.M., et al., 1998, *Clinical Cancer Research* 5:1125–1134 "In Vivo Toxicity Pharmacokinetics and Anti–Cancer Activity of Genistein Linked to Recombinant Human Epidermal Growth Factor".

Ueda, M., et al., 1995, *Coron. Artery Dis.* 6,71–81 "Smooth Muscle Cell De–differentiation is a Fundamental ChangePreceding Wound Healing After Percutaneous Transluminal Coronary Angioplasty in Humans".

Vaitkus, P.T., 1995, *Coron. Artery Dis.* 6, 429–439 "The Continuing Evolution of Percutaneous Transluminal Coronary Angioplasty in the Treatment of Coronary Artery Disease".

Wright, J.D., et al., 1995, *J. Biol. Chem.* 270, 12085–12093 "An Incomplete Program of Cellular Tyrosine Kinase Phosphorylation by Kinase—Defective Epidermal Growth Factor Receptors".

Ahmad, N. et al., "Skin Cancer Chemopreventive Effects of Flavonoid Antioxidant Silymarin Are Mediated via Impairment of Receptor Tyrosine Kinase Signaling and Perturbation in Cell Cycle Progression," *Biochemical and Biophysical Research Communications*, vol. 248, No. 2, pp. 294–301 (1998).

Baguley, B.C. et al., "Inhibition of Growth of Primary Human Tumor Cell Cultures by a 4—Anilinoquinazoline Inhibitor of the Epidermal Growth Factor Receptor Family of Tyrosine Kinases," *European Journal of Cancer*, vol. 34, No. 7, pp. 1086–1090 (1998).

Levitzki, A. et al., "Tyrosine Kinase Inhibition: An Approach to Drug Development," *Science*, vol. 267, pp. 1782–1788 (Mar. 24, 1995).

Mattar, T. et al., "Inhibition of the epidermal growth factor receptor tyrosine kinase activity by leflunomide," *Febs. Letters*, vol. 334, No. 2, pp. 161–164 (Nov. 1993).

Srivastava, A.K., "Inhibition of Phosphorylase Kinase, and Tyrosine Protein Kinase Activities by Quercetin," *Biochemical and Biophysical Research Communications*, vol. 131, No. 1, pp. 1–5 (Aug. 30, 1985).

Wakeling, A.E. et al., "Specific inhibition of epidermal growth factor receptor tyrosine kinase by 4—anilinoquinazolines," *Breast Cancer Research and Treatment*, vol. 38, pp. 67–73 (1996).

Xu, X. et al., "Two Activities of the Immunosuppressive Metabolite of Leflunomide, A77 1726," *Biochemical Pharmacology*, vol. 52, pp. 527–534 (1996).

*Primary Examiner*—F. T. Moezie
*Attorney, Agent, or Firm*—Merchant & Gould P.C.

[57] ABSTRACT

A protein conjugate containing EGF coupled to a tyrosine kinase inhibitor such as Genistein, for inhibiting or preventing restenosis following vascular injury.

19 Claims, 7 Drawing Sheets

EGF-ISOFLAVONE CONJUGATES FOR THE PREVENTION OF RESTENOSIS

FIELD OF THE INVENTION

This invention relates to a method for preventing and treating vascular restenosis due to vascular injury by administering a conjugate formed of EGF and an isoflavone tyrosine kinase such as Genistein. More particularly, the invention relates to the use of EGF-Genistein to prevent the migration and proliferation of myofibroblasts and to prevent formation of neointima, thereby preventing and/or treating restenosis due to vascular injury, particularly vascular injury due to medical procedures such as angioplasty.

BACKGROUND OF THE INVENTION

Revascularization of obstructed coronary arteries by percutaneous transluminal coronary angioplasty (PTCA) has become an integral component of front-line treatment programs for patients with ischemic heart disease (Vaitkus, P. T. 1995, *Coron. Atery Dis.,* 6:429–439). Although acute complications of PTCA have markedly declined with optimized use of anticoagulants, antispasmodic agents, and intravascular stents, the incidence of coronary artery restenosis has remained at 30%–50% and represents the major obstacle to a more successful outcome of PTCA (Landzberg, et. al., 1997, *Prog. Cardiovascular Diseases,* 39:361–298). Therefore, the development of effective strategies for restenosis prophylaxis has become a focal point for translational cardiovascular research.

The pathogenesis of restenosis has been compared to an exaggerated wound healing response with migration of smooth muscle cells from the media to the intima of the revascularized coronary artery where they proliferate and cause an obstructive neointimal hyperplasia (Ueda et al., 1995, *Coron. Artery Dis.,* 6:71–8 1). Many factors contribute to the development of restenosis, including vascular injury, platelet aggregation, procedural factors, inflammation, and mitogenic stimulation of migration and proliferation of smooth muscle cells. The relative contribution of any one of these factors remains unclear.

Pharmacological approaches to prevent restenosis include antiplatelet and antithrombotic agents, anti-inflammatory drugs, growth factor antagonists, vasodilators, antiproliferatives, antineoplastics, photochemotherapy, and lipid lowering agents. Some growth factor antagonists have also been studied for effects on restenosis.

Inhibition of vascular smooth muscle cell proliferation by a platelet derived growth factor (PDGF)-antagonist has generated promising results in preclinical as well as early clinical studies, thereby confirming the biologic importance of vascular smooth muscle cells in the pathophysiology of restenosis (Mullins et al., 1994, *Arterioscler. Thromb.,* 14:1047–1055).

Targeting Genistein (Gen) (5,7,4'-trihydroxyisoflavone), a naturally occurring tyrosine kinase inhibitor present in soybeans (Aikyama ET.AL., 1987, *J. Biol. Chem,* 262:5592–5595; Uckun et al., 1995, *Science* 267:886–891) to the EGF-receptor/PTK complexes in breast cancer cells using the EGF-Gen conjugate resulted in marked inhibition of the EGF-receptor tyrosine kinase and EGF-receptor-associated Src family PTK (Uckun et al., 1998, *Clinical Cancer Research,* 4: 901–912).

Figure 1:
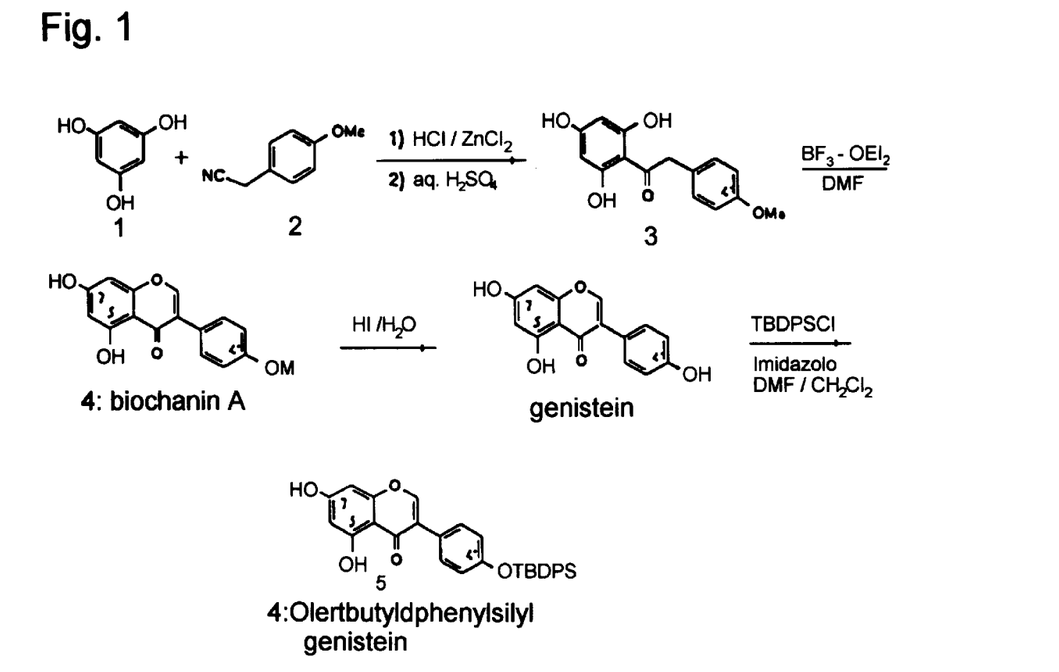
FIG. 1 is a schematic representation of a two step photochemical method for the synthesis of Genistein.

Proliferating vascular smooth muscle cells also express high levels of the EGF-receptor (Saltis et.al., 1995, *Atherosclerosis,* 118:77–87). Furthermore, as described more fully in the Examples below, a noninvasive small animal model of restenosis (FIG. 1), which employs photoactivated rose bengal to induce vascular injury to the femoral arteries of C57B 1/6 mice leading to neointimal hyperplasia mimicking the post-PTCA restenosis of coronary arteries, demonstrated that the myofibroblasts of the neointima were EGF-receptor positive in 8 of 8 mice (100%) analyzed. Notably, the neointima of the injured femoral arteries stained more intensely with the anti-EGF receptor antibody than the media and/or intima of uninjured femoral arteries.

These findings suggested that the EGF-receptor function and EGF-receptor-linked signal transduction events may be essential for the migration and proliferation of myofibroblasts contributing to the neointimal hyperplasia after vascular injury. It was then postulated that the EGF-receptor on vascular smooth muscle cells may be a suitable target for restenosis prophylaxis using EGF-receptor-directed tyrosine kinase inhibitors such as EGF-Genistein.

Development of prevention and treatment methods for vascular restenosis remains an important goal of cardiovascular research. Currently there are very limited treatment options available to prevent or treat restenosis, particularly following PTCA. Accordingly, there is a need for specific and effective therapeutic treatments for the inhibition of restenosis, particularly for patients undergoing coronary angioplasty.

Several animal models have been developed for studying restenosis. Major blood vessels of rats, rabbits and pigs have been subjected to injury from balloon or stent mediated treatment. Porcine coronary arteries seem to be the most predictive of the human response. However, many of these models are not amenable to large scale screening of prophylactic or therapeutic agents. Accordingly, an animal model of restenosis that can be used for large scale screening of therapeutic and prophylatic agents is needed.

SUMMARY OF THE INVENTION

The invention provides a method for preventing and/or treating restenosis. In particular, administration of a compound comprising an isoflavone tyrosine kinase inhibitor (ITKI) conjugated to EGF is effective to suppress migration of vascular smooth muscle cells and formation of hyperplastic neointima in response to vascular injury. Accordingly, the invention includes a method for inhibiting the migration and proliferation of vascular cells and for inhibiting the formation of neointima. In particular, the invention includes a method for the inhibition or prevention of restenosis by administration of an isoflavone tyrosine kinase inhibitor-EGF conjugate such as EGF-Genistein. In a preferred embodiment, the EGF-ITKI. The invention also includes a novel animal model effective for large scale screening of agents effective in preventing and treating restenosis.

DETAILED DESCRIPTION OF PREFERRED EMBODIMENTS

The invention provides methods for the prevention and/or treatment of vascular restenosis, including the prevention and treatment of neointimal hyperplasia induced by vascular injury. The invention also provides an animal model of restenosis for screening of prophylactic and therapeutic agents effective in preventing and ameliorating the symptoms of restenosis.

Restenosis

For purposes of this invention, restenosis is defined as a tissue response to vascular injury and includes the symptoms of migration and proliferation of smooth muscle cells to the site of vascular injury and the formation of neointimal hyperplasia in the damaged vessel.

As used herein, "induction of vascular injury" is meant to include application of clinical treatments and/or procedures known to induce vascular injury and to promote the development of restenosis. Examples of such clinical treatments and/or procedures include various types of angioplasty procedures, such as PCTA.

Protein Tyrosine Kinase Inhibitors

Isoflavone tyrosine kinase inhibitors (ITKI) are known, and are described, for example, in U.S. patent application Ser. No: 08/602,186. Representative examples include a preferred ITKI of the invention, Genistein.

Genistein, an isoflavone (5,7,4'-trihydroxyisoflavone) derived from the fermentation broth of Pseudomonas species, is a naturally occurring, specific tyrosine kinase inhibitor present in soy beans, soy meal and tofu (Akiyama, et al., 1987, *J. Bio. Chem.*, 272:5592). Genistein is a fairly specific inhibitor for tyrosine kinases, having negligible inhibition activity against serine and threonine kinases (Ogawara, et al., 1986, *J. Antidote. (Tokyo)*, 39:606). Genistein is generally known as a weak inhibitor of tyrosine kinase, which only reversibly inhibits tyrosine kinase. Genistein and similar isoflavones do not easily enter cells and the delivery of the ITKIs to cells in non-toxic doses presents problems for therapeutic use. Conjugation of Genistein to EGF was shown to inhibit the EGF receptor tyrosine kinase in breast cancer cells leading to apoptosis and cell death. The potency of the conjugate was 1000-fold greater than unconjugated Genistein. Thus, Genistein, targeted to specific EGF responsive cells by conjugation to the EGF receptor, was converted into an effective anti-cancer agent (U.S. patent application Ser. No. 08/602,186).

Daidzein (7,4'-dihydroxyisoflavone), other isoflavones isolated from soy, and biochanin A (4-methoxygenistein) are examples of additional isoflavone tyrosine kinase inhibitors that have been shown to inhibit proliferative growth of human breast cancer cell lines (Peterson, et al., 1991, *BBRC* 179:661–667).

Genistein has been shown to prevent apoptosis in cells which have undergone ionizing radiation or engagement of the CD 19 receptor (Uckun, et al., 1992, *P.N.A.S. USA*, 89:9005). Genistein may be obtained commercially from Calbiochem (LaJolla, Calif.). Alternatively, Genistein may be isolated from soybeans, soy meal or tofu by the method described in Akiyama, et al. (*J. Bio Chem.*, 1987, 272:5592). Genistein is preferably synthesized by the method described in U.S. patent application Ser. No. 08/602,186.

Epidermal Growth Factor (EGF) and Its Receptor (EGF-Rc)

Human Epidermal Growth Factor is a 53 amino acid, single-chain, 6216 dalton peptide, which exerts biological effects by binding to a specific 170 kDa cell membrane receptor, EGF-receptor/ErbB-1 (EGF-Rc). The human EGF-Rc consists of an extracellular domain with a high cysteine content and N-linked glycosylation, a single transmembrane domain, and a cytoplasmic domain with protein tyrosine kinase (PTK) activity. Binding of EGF to the EGF-Rc results in receptor dimerization with itself or other members of the ErbB (subtype I) transmembrane PTK family (including Erb-B2 and Erb-B3), resulting in activation with autophosphorylation of the PTK domain. The EGF-Rc is physically and functionally associated with the Src protooncogene family PTK including p60 src (Muthuswamy, S. K., 1994, *Molecular & Cellular Biology*, 14:735–743; Ottenhoff-Kalffet al., 1992, *Cancer Research*, 52:4773–4778; Aikyama et al., 1987, *J. Biol. Chem.*, 262:5592–5595). This association is believed to be an integral part of the signaling events mediated by the EGF-Rc. Activation of proliferative pathways by PTKs has been suggested as playing a role in the development and progression of various types of human cancer.

EGF is commercially available in a highly purified form; for example, from Upstate Biotechnology, Inc. (Lake Placid, N.Y.) (Lot No. 01-107C). This protein ligand is known to bind specifically and with high affinity to receptors located on the surface of EGF-responsive cells. Expression of the EFG-Rc is increased in EGF-responsive cells, including hyperplastic neointima cells.

For use in the conjugates of the present invention, recombinant human EGF (hrEGF) is preferred, although it is anticipated that HEGF and HEGF analogs that specifically bind hEGF-Rc on neointima cells and will similarly deliver the conjugated ITKI to target cells and similarly inhibit migration of vascular cells and formation of hyperplastic neointima cell growth.

Production and Purification of EGF-Genistein Conjugates

Preferred conjugates of the invention are formed by linking an effective amount of isoflavone tyrosine kinase inhibitor, such as Genistein molecules, to each molecule of EGF. For example, a reagent useful in the practice of the invention is a composition containing at least a 1:1 molar ratio of EGF:Genistein, that is, having at least one Genistein molecule per EGF molecule. Preferably, the conjugate contains at least a 1:3 molar ratio of EGF:Genistein, that is, having at least three Genistein molecules per EGF molecule. The published photochemical conjugation method used for preparation of a B43-Genistein immunoconjugate reported in Uckun, et al. (*Science*, 1995, 267:886) can be employed to generate an EGF-genistein conjugate.

One method for preparing the EGF-ITKI conjugate of the invention involves a two-step procedure, using the heterobifunctional photoreactive linking agent Sulfo-SANPAH (Pierce Chemical Co., Rockford, Ill.), which contains an N-hydroxysuccinimidyl ester and an m-nitro aryl azide on either terminus, as described in U.S. patent application Ser. No. 08/602.186. In the first step, incubation of the purified rhEGF with Sulfo-SANPAH at a 10:1 molar ratio of Sulfo-SANPAH:rhEGF forms amide linkages between free amino groups and the activated succinimidyl ester of Sulfo-SANPAH. Excess bifunctional linker is removed, e.g., by size-exclusion chromatography. Photolytic generation of a reactive singlet nitrene on the other termilnus of the bifunctional linker in the presence of a 10-fold molar excess of genistein in DMSO then covalently incorporates the genistein into the conjugate at each of the three lysine residues. The singlet nitrene intermediate that was generated upon exposure to longwave UV light is preferentially inserted into the oxygen-hydrogen bonds of the C7-hydroxyl group of genistein. Excess genistein is removed, e.g., by size-exclusion chromatography.

It is commonly known to those skilled in the art that an isoflavone, such as genistein, can be modified to produce an amino-isoflavone which can be linked to proteins such as EGF using common bifunctional linking agents. Such common bifunctional linking agents would include, for example, M-succinimidyl 3-(2-pyridyldithio)propionate, 4-Treatment, 35:115–132; Wright, et al., 1995, *J. Biol. Chem.*, 270:12085–12093; Broome and Hunter, 1996, *J. Biol Chem*, 271:16798–16806). The human EGF-receptor consists succinimidyloxycarbonyl-methol-(2-pyridyldithio)-toluene, and N-succimidyl 6-[3-(2-pyridyldithio)propionamido] hexanoate.

Administration of EGF-Genistein

The conjugates of the present invention are preferably formulated as pharmaceutical compositions adapted to a chosen route of administration. Preferred administration routes include oral, intravenous, intramuscular, intraperitoneal, subcutaneous, or locally delivered via an implantable device.

It is preferred that the conjugate of the present invention be administered parenternally, i.e., intravenously or intraperitoneally, by infusion or injection. Solutions or suspensions of the conjugates can be prepared in water, isotonic saline (PBS) and optionally mixed with a non-toxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as a glycerol, propylene glycol, or liquid polyethylene glycols, and the like, vegetable oils, nontoxic glyceryl esters, and suitable mixtures thereof. The fluidity can be maintained, for example, by the formation of liposomes, by the maintenance of required particle size in the case of a dispersion, or by the use of nontoxic surfactants. The prevention of the action of microorganisms can be accomplished by various antibacterial and antifungal agents, for example, parabens, chlorobutanol, sorbic acid, thimeosal and the like. In many cases, it will be desirable to include isotonic agents, for examples, sugars, buffers or sodium chloride. Prolonged absorption of the injectable compositions can be brought about the inclusion in the composition of agents delaying absorption, for example, aluminum monostearate hydrogels and gelatin.

One preferred route of administration is via local delivery using an implantable reservoir adjacent to surfaces of the injured blood vessel, especially those placed percutaneously. The advantages of locally delivery include the use of high concentration of drug while minimizing side effects, and prolonged administration of the drugs. Devices that could be utilized include porous and infusion balloon catheters, stents, techniques for facilitated diffusion and coated microspheres. Other preferred routes of administration include intravenous routes or parenteral routes of administration.

The EGF-genistein conjugates can be administered alone or in combination with other therapies, for example, it may be desirable to also administer the conjugates of the invention with an anti-inflammatory agent or with an antiplatelet or antithromotic agent.

The EGF-Genistein conjugates can be administered before, during and after a vascular injury. Vascular injuries occur in human patients, for example, after medical procedures such as coronary angioplasty. These percutaneous procedures are conducted on patients with stable angina with single vessel disease, as well as those with multivessel disease, total occlusion, complex lesions, unstable angina and acute myocardial infarction. Several procedures in common use today can result in vessel injury, and would benefit from the method of the invention. These include balloon angioplasty, vessel stents, rotational and directional atherectomy, and laser angioplasty.

In a preferred embodiment, a patient is pretreated with EGF-ITKI such as EGF-genistein conjugate at least one to three days before the treatment or procedure which is known to induce vascular injury. For example, it is preferred that administration of an EGF-Genistein conjugate is performed one to three days before a medical procedure such as PTCA. Delivery of the EGF conjugate continues after the vascular injury or medical procedure up to a period of about 2 weeks to 6 months post injury. The conjugate is preferably administered to the patient for a period of about 1 month to 3 months post injury. It is believed that the period 1 month to 3 months is the time at which restenosis formation peaks after a vascular injury.

However, often the pretreatment option is not available to patients in an emergency situation. An emergency situation may arise requiring a medical procedure that causes vascular injury. In that situation, the EGF-IFKI conjugate can be administered during the procedure and/or after the procedure. The EGF conjugate can be administered for a period after injury of 2 weeks to about 6 months, preferably at least 1 to 3 months.

The administration of the EGF conjugates ameliorates or prevents development of restenosis. Some level of neointima hyperplasia can still be present in those patients treated with EGF-genistein conjugates but the formation of neointima is significantly ameliorated compared to untreated patients. Treatment course and dose of the EGF conjugates can be adjusted in the patient if the clinical signs indicate a need for increased dose or treatment time.

Methods for analysis of restinosis are known, and include, for example, quantitative coronary angiography (QCA), where narrowing of a vessel is visualized by injection of a visualizing dye. Another method for analyzing restinosis is by intravascular ultrasound imaging (IVUS). By inserting the ultrasound probe into a vessel, the diameter of the vessel, as well as the type and extent of lesions in the vessel can be analyzed.

Dosage

The amount of EGF-genistein conjugate administered is an amount effective to prevent, inhibit or ameliorate the symptoms of restenosis. Preferred doses are those that are 10% or less of the highest cumulative nontoxic dose. The doses of the conjugates to be administered can vary widely in accordance with the size, age, and condition of the patient to be treated.

Useful dosages of the conjugates are those which will yield systemic exposure levels (i.e., area under serum concentration×time curve) of 0.28 micrograms/liter per hour or greater. Systemic exposure levels can be optimized in an individual patient by simply adjusting the dose according to the measured conjugate concentrations in the serum. Based on the monkey pharmacology data contained in this application, effective exposure levels are expected to be achieved with doses as low as 25 micrograms/kg. It will be understood by one in the field that lower or higher doses may be useful, depending upon the specific treatment conditions.

Preferably, a cumulative dose of the conjugate of the invention is less than about 140 mg, more preferably is less than about 50 mg/kg, and most preferably is less than about 5 mg/kg. A dose of about 1 to 5 milligram per kilogram is preferred. Effective exposure levels can be achieved with doses as low as 25 micrograms/kg. Systemic exposure levels can be optimized in the patient by adjusting the dose according to the levels of conjugate measured in the serum. Doses may also be adjusted depending on whether a local delivery method is utilized.

Screening, Methods for Identifying Agents that Inhibit Vascular Restenosis

Methods of the invention also include the development of an animal model that allows for high throughput in vivo screening of agents that prevent, inhibit, or ameliorate the symptoms of restenosis. Current animal models include rats, rabbits and pigs. The porcine model is thought to be the closest to the human vascular system. The drawbacks of the current animal models are that it is hard to do large volume in vivo screening of agents, and the procedures for inducing vascular injury are time consuming.

A method of the invention involves inducing vascular injury in a mouse, administering the inhibitory agent to the mouse, and determining whether the agent inhibits restenosis in the mouse after the injury.

The mouse is preferably a C57B1/6 mouse. The mice have also preferably been fed a diet that substantially elevates their cholesterol levels before and after injury is induced. A preferred diet is the Paigen's cocoa butter diet and is preferably administered for at least 2 weeks prior to injury.

Vascular injury can be induced in a variety of ways. A major blood vessel of the mouse, such as the aorta can be exposed to invasive procedures similar to angioplasty. Alternatively, a photoactivated rose bengal solution or other chemical agents can be utilized to cause injury to the vessel wall. (See, for example, agents listed in Table 1 of Fritsch et al., 1998, *Arch. Dermatol.* 134: 207–214.) In a preferred embodiment, photoactivated rose bengal is administered to the mouse, and the mouse is irradiated at the left femoral artery to induce vascular damage.

An agent suspected of inhibiting development of restenosis can be administered after the vascular injury is induced. Administration can occur intraperitoneally, intravenously, peritoneally, subcutaneously or locally through an implantable device. A range of doses can be utilized to determine the optimal dose range of the particular inhibitory agent. Dose ranges are preferably well below (i.e., less than 10%) toxic levels. Preferred ranges of doses may be .01 mg/kg to 1 mg/kg and more preferably 0.01 mg/kg to 0.1 mg/kg.

The agent can be administered for about 2 weeks to 4 weeks after vascular injury. In the mouse model as described herein, neointima hyperplasia is seen as early as two weeks after injury and in all of the mice at four weeks after injury. The agent can be administered one or more times a day. In an alternative embodiment, the mouse may be pretreated with the agent at least one to three days before vascular injury is induced.

The inhibition of development of vascular restenosis upon treatment with the agent can be determined by examination of the injured blood vessel. The injured blood vessel can be excised, serial sectioned and stained for histomorphometric analysis. Imaging programs such as the NIH 1.61 program can be utilized to analyze the sections. (Rasband et al., 1995, *Microbeam Analysis Soc. J.* 4:137–149.) A stenosis index can be calculated by determining the media/intima ratio. A decrease in the stenosis index compared with control animals indicates that the agent inhibits or prevents restenosis. Significant amelioration or inhibition of the formation of neointima hyperplasia by the agent indicates the agent can be useful to ameliorate, inhibit or prevent restenosis after vascular injury.

EXAMPLES

The invention may be further clarified by reference to the following Examples, which serve to exemplify some embodiments, and not to limit the invention.

Example 1

Preparation and Characterization of EGF-Genistein Conjugate

The published photochemical conjugation method for preparation of the B43-Gen conjugate as described in Uckun et al., *Science,* 267:886–891 (1995), was employed to generate an EGF-Gen conjugate. This method involves a two-step procedure using the heterobifunctional photoreactive cross-linking agent Sulfo-SANPAH, which contains an N-hydroxy-succinimidyl-ester and m-nitro aryl azide on either terminus. (optimal photolysis is at 265–400 nm) The reaction procedure is shown FIG. 1. In the first step, highly purified, endotoxin free rhEGF (Upstate Biotechology, Lake Placid, N.Y.) was incubated with a 40 nM solution of Sulfo-SANPAH in DMSO (Pierce Chemical Company, Rockford, Ill.) at a 10:1 molar ratio of sulfoSANPAH: rhEGF to form amide linkages between free amino groups and the activated n-hydroxy-succinimidyl-ester of the sulfoSANPAH. Excessive linking agent was removed by passing the reaction mixture through a PD-10 prepacked D25 column (Pharmacy at LKB, Piscataway, N.J.). Photolitic generation of a reactive singlet nitrine on the other terminus of the EGF linking agent in the presence of a 10-fold molar excess of 50 mM genistein in DMSO (Gen; Molecular Weight 270.2, Calbiochem, Lahoya, Calif.) covalently incorporated the genistein into the conjugate. The mixture was irradiated with gentle mixing for 10 minutes with UV light at wavelengths of 254–366 nanometers using a multi-band UV light emitter (Model UVGL-15 mineral light, UVP San Gabriel, Calif.). The singlet nitrine intermediate was generated upon exposure to long-wave ultraviolet (UV) light and was preferentially inserted into the oxygen hydrogen bonds of the C7 hydroxyl group of genistein. Excessive genistein was removed by passage through a PD-10 column.

Other tyrosine kinase inhibitors that were included as controls were unconjugated Genistein, 4-(3',5'-dibromo-4'- hydroxyphenyl)-amino-6,7-dimethoxyquinazoline, 4-(4'hydroxylphenyl)-amino-6,7 dimethoxy quinazoline, and 4-(6'-hydroxylphenyl)-amino-6, 7-dimethoxy quinazoline (kindly provided by Dr. X- P. Liu, Alexander Park Pharmaceuticals, Inc., Roseville, Minn.)

The chemical composition and biological activity of EGF-genistein in vitro have been previously characterized in Uckun et al., 1988, Clin. Cancer Res. 4:901–912, "Cytoxic Activity of EGF-Genistein against human breast cancer cells."

Example 2

Murine Restenosis Model

Figure 2A:
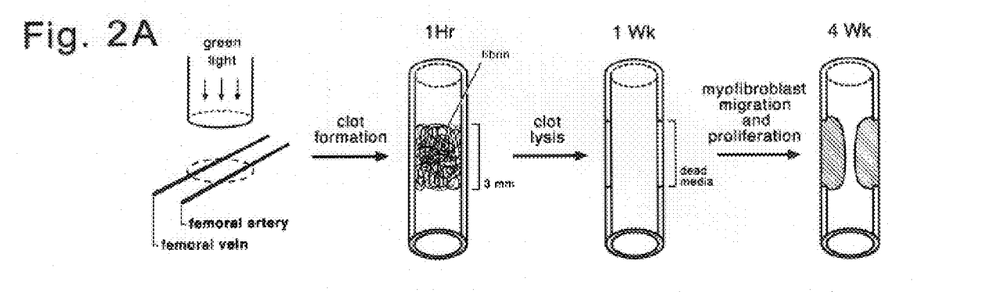
FIG. 2A is a schematic illustration of an experimental model of vascular injury-induced neointimal hyperplasia.

A model of vascular restenosis was developed in mice using photoactivated rose bengal to induce vascular injury to the femoral arteries of mice. This injury results in neointimal hyperplasia within 2–4 weeks. The scheme for experimental mouse model of vascular injury induced neointimal hyperplasia is shown in FIG. 2A.

Photoactivation of rose bengal, a xanthene-type dye structurally related to fluorescein, results in the generation of reactive oxygen intermediates. Percutaneous irradiation of one femoral artery with a green light source following intravenous administration of rose bengal results in blood vessel injury evidenced by destruction of the vascular endothelium. The denuded vessel wall triggers platelet aggregation and thrombus formation at the site of vascular injury. After injury, there is a progression from clot formation, through necrosis, to formation of neointima in the mouse model of restenosis.

Three to four week old C57 B1/6 male mice (Taconic, Germantown, N.Y.) were housed in micro-isolator cages on a 12-hour day/night cycle and kept for 2 weeks on the Paigen's cocoa butter diet of 15.8% fat, 1.25% cholesterol and 0.5% sodium cholate (Harlan Teklad, Madison, Wis., U.S.A.) to induce high plasma cholesterol levels similar to those of patients with lipid disorders. Plasma cholesterol levels are shown in Table 1.

TABLE 1

| Time | Plasma Cholesterol Level |
| --- | --- |
| 0 week | 125 ± 21 mg % (n = 12) |
| 1 week | 346 ± 62 mg % (n = 5) (p < 0.0001) |
| 2 weeks | 370 ± 60 mg % (n = 30) |
| 3 weeks | 371 ± 64 mg % (n = 29) |
| 4 weeks | 267 ± 91 mg % (n = 29) |
| 5 weeks | 337 ± 101 mg % (n = 27) |
| 6 weeks | 353 ± 71 mg % (n = 26) |

Plasma cholesterol levels increased from 125±21 mg % to 346±62 mg % after one week on the cocoa butter diet. The elevated cholesterol level remained relatively constant throughout the time.

Mice were injected with 300 microliters of a 3 mg/ml photoactivated rose bengal solution (Aldrich, Milwaukee, Wis.) in sterile PBS via the tail vein and anesthetized with ketamine/xylazine solution (100 mg ketamine/kg and 5 ml xylazine/kg). Photoactivation of rose bengal using percutaneous irradiation with a green light source (300 Watt Xenon arced lamp equipped with a 550 nanometer broad band interference filter, Oriel Scientific, Stratford, Conn.) was performed on the shaved left leg by placing a 3.2 mm glass fiber optic light guide directly into the left femoral vein/artery for 10 minutes. The unirradiated right femoral artery served as an internal control.

Following irradiation the mice were treated for either 14 days or 28 days with intraperitoneal injections of (1) EGF-Gen conjugate or unconjugated EGF (modified EGF not conjugated to genistein) at a dose level of 0. I mg/kg/dose once in the morning and once in the evening; or (2) 2 mg/kg/dose of unconjugated genistein or derivatives of 6,7-dimethoxyquinizalone dissolved in 10% DMSO once per day; or (3) with PBS.

At the times indicated, the animals were euthanized with ketamine/xylazine and perfused with PBS followed by 4% phosphate buffered formalin. PBS and formalin were pumped through the left ventricle of the heart and allowed to exit through a 3 mm incision through the interior wall of the right ventricle. The brain, thymus, heart, lung, liver, pancreas, kidney, spleen, intestine, stomach, muscle, skin adrenal, and testes were collected for pathological evaluation. For histopathological studies, tissues were fixed in 10% neutral buffered formalin, dehydrated and embedded in paraffin by routine methods. Tissue blocks containing the femoral artery/vein were excised and post-fixed in 4% phosphate buffered formalin overnight and processed for hemotoxylin and eosin (H&E) or Masson's trichrome staining. Glass slides were affixed with 6 micron tissue sections and were stained with hematoxylin and eosin or Masson's trichrome. Serial sections were examined for areas of maximum neointimal hyperplasia for which the ratios of neointima/media (stenosis index) were determined. This was necessary to compensate for angular differences among specimens. A Pixera camera (Pixera Corp., Calif., USA) was used for image capture and the NIH image 1.61(Rasband et al., 1995, Microbeam Analysis Soc. J. 4:137–149) program was used for histo-morphometric analysis.

All numeric data are shown as mean±SEM. Statistical analysis between groups was performed by Mann-Whitney t-test or Fisher's exact test using Instat, GraphPad Software, San Diego, Calif. Cumulative percentage plots were analyzed using Wilcoxon statistics by Statview, Abacus Concepts, Inc., Berkeley, Calif.

Figure 2B:
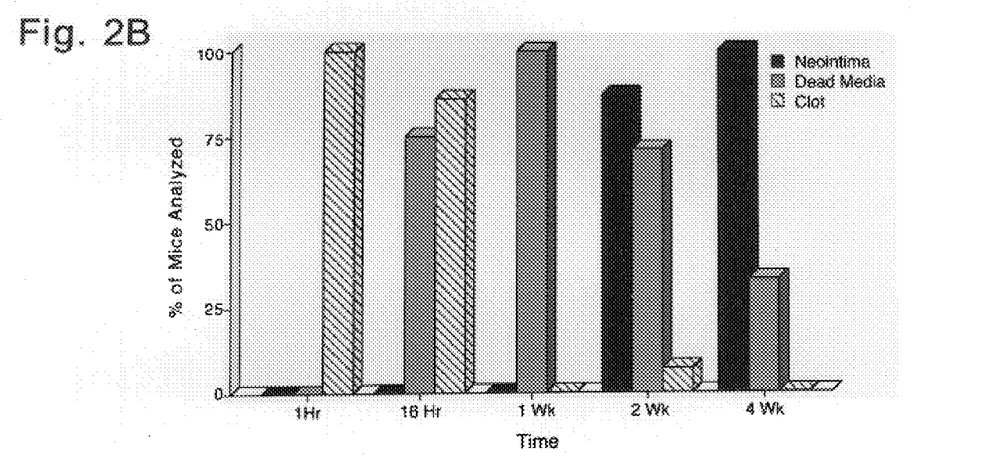
FIG. 2B is a bar graph showing progression of neointima following vascular injury in the mouse model of restenosis.
Figure 2C:
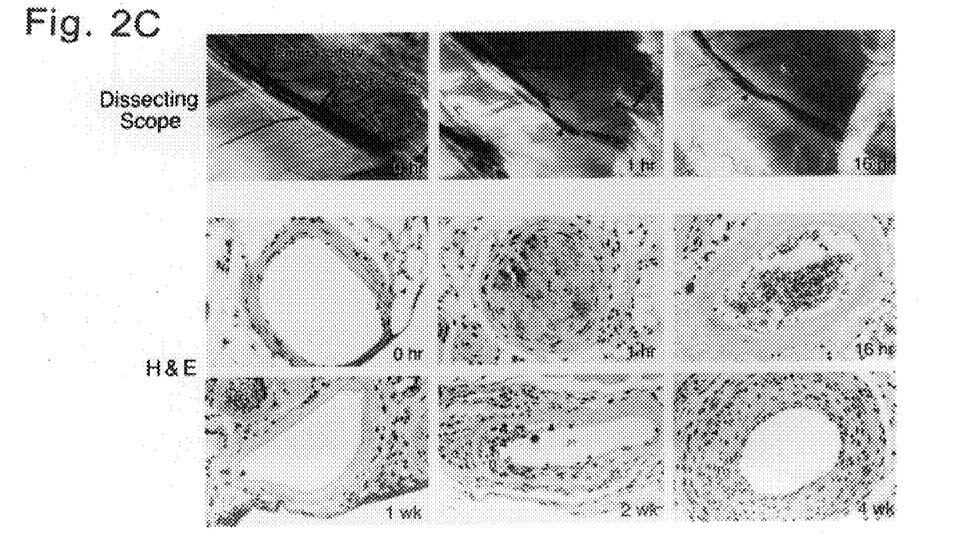
FIG. 2C is a panel of photographs showing microscopic progression of restenosis following vascular injury in the murine animal model.

The results in FIG. 2 show that the small animal model of restenosis employing photoactivated rose bengal to induce vascular injury to the femoral arteries of mice leads to neotima hyperplasia that mimics the post-PTCA restenosis of coronary arteries.

In FIG. 2B, the injured femoral arteries were scored for the presence of neointima, dead media, or clot at 1 hour (n=2), 16 hours (n=8), 1 week (n=4), 2 weeks (n=15), and 4 weeks (n=45) and the percentage of animals scored positive are shown. The results showed that 2 weeks after irradiation, neointima formation is present and that neointima formation is readily detectable at 4 weeks post irradiation period. Clot formation was present in the first 24 hours after irradiation, but disappeared by 1 week post irradiation. Dead media cells were detected within the first 24 hours, but decreased by 4 weeks post irradiation.

These data correlate with progression of stenosis seen in human disease, including endothelial denaturation, thrombus, medial necrosis and VSMC (myofibroblast) migration and proliferation.

FIG. 2C shows a microscopic analysis of this murine model of restenosis. Sections of femoral artery were stained with hematoxylin and eosin at various time periods post irradiation (400×magnification). The panels in FIG. 2C show the development of a clot in the femoral artery at one hour, followed by dissolution of the clot around 16 hours post irradiation. In the bottom panels, the formation of a neointima hyperplasia is seen as time progresses from 1 week to 2 weeks to 4 weeks post irradiation. Arrows indicate the internal elastic laming Neointima (n) and thrombus (t) are indicated.

Within 10 minutes after irradiation, the femoral artery was occluded by a visible 3 mm long thrombus in 8 of 8 mice (100%). The adjacent femoral vein also collapsed, but this was due to vasoconstriction rather than an occluding thrombus. Venous blood flow was usually restored within a few days after irradiation with no histopathological evidence of an injury. Even 16 hours after irradiation, the femoral artery was clot occluded in 7 of 8 mice (88%) examined. The occlusive thrombus in the femoral artery underwent fibrinolysis with complete restoration of arterial blood flow in the majority of mice. Occlusive thrombi were found in none of the 3 mice (0%) examined at 1 week, only 1 of 15 mice (7%) examined at 2 weeks and none of the 45 mice (0%) examined at 4 weeks.

At 16 hours, concomitant with the fibrinolysis of the occluding clot, the media of the injured femoral artery became necrotic with the disappearance of smooth muscle cells in 6 of 8 mice (75%) examined. The media was eventually repopulated by an influx of highly proliferative myofibroblasts and the frequency of microscopically detectable media necrosis progressively decreased from 100% (3 of 3 mice) at 1 week to 80% (12 of 15 mice) at 2 weeks, and 33% (15 of 45 mice) at 4 weeks (p=0.0024, 2 weeks vs. 4 weeks, Fisher's exact test). Neointima formation was excessive and pericentric neointimal hyperplasia was observed in 13 of 15 mice (87%) at 2 weeks and 45 of 45 mice (100%) at 4 weeks after vascular injury. After 4 weeks, there was significant accumulation of collagen and extracellular matrix material to give the neointima a blue color after staining with Masson's trichrome.

The results as shown in FIG. 2 indicate that this mouse model can be used as a model for vascular restenosis. This experimental model of restenosis in mice may facilitate the development and optimization of novel strategies for restenosis prophylaxis since it is amenable to high throughput in vivo screening of new agents and new agent combinations.

Example 3

Detection of EGF-Receptor Expression in Neointimal Hyperplasia

Serial tissue sections were evaluated for the presence of α-actin and EGF-receptor by immunostaining. The presence of α-actin serves as a marker of vascular smooth muscle cells. Proliferating vascular smooth muscle cells were examined for expression of the EGF-receptor.

Injury to the femoral artery of C57B1/6 mice was induced according to the method described for Example 2. Animals were euthanized with ketamine/xylazine and perfused with PBS followed by 4% phosphate buffered saline. Tissue blocks containing the femoral arteries/vein were excised and post fixed in 4% phosphate buffered formalin overnight. Paraffin embedded sections were washed three times, 10 minutes each in Hemo-De (Fischer Scientific, Pittsburgh, Pa.), rinsed in absolute ethanol, then treated with 0.5% hydrogen peroxide in methanol for 30 minutes. The slides were then washed in water, incubated in PBS-Tween (PBS with 0.1% Tween 20) for 10 minutes, followed by blocking in 10 % FBS in Dulbecco's Modified Essential Medium (DMEM) for one hour.

For visualization of the EGF-receptor, the sections were incubated for one hour with a 10 ug/ml solution of a rabbit polyclonal antibody against mouse EGF-receptor (epitope mapping at residues 1,005 to 1,016; Santa Cruz Biotech, Santa Cruz, Calif.). For visualization of α-actin, the sections were incubated with a 1:100 dilution of clone 1 A4 mouse ascites fluid containing a monoclonal anti-α-actin antibody raised against the amino terminal decapetide of human α-actin (Sigma, St. Louis, Mo.). Horseradish peroxidase conjugated anti-rabbit or anti-mouse antibodies (1:100 dilutions, 1 hour incubation; Pierce, Rockford, Ill.) were used as secondary antibodies.

Sections were washed in PBS-Tween and incubated for 10 minutes in the substrate solution of 100 μl of a stock solution of 3-amino-n-ethylcarbazole in N'N'-dimethylformamide at 2.4 mg/ml, (Sigma, St. Louis, Mo.) 1 ml of acetate buffer pH 5.2, and 5 μl of 30% w/w hydrogen peroxide. Sections were then counterstained with Mayer's Hemotoxylin and mounted using crystal mount (Biomeda Corp., Foster City, Calif.). A monoclonal mouse anti-human collagen IV (Clone CIV 22. Dako Corp., Carpinteria, Calif.) and rabbit polyclonal antibody raised against a human EGF-peptide (CalBioChem, LaJolla, Calif.) were used as control antibodies.

The cellular elements of the hyperplastic neointima generated after vascular injury were positive for alpha actin, a marker for vascular smooth muscle cells (i.e., myofiberblasts) in 7 of 7 mice analyzed (100%). Among these immunocytochemically identified myofibroblasts of the neointima, those closest to the lumen were spindle-shaped, longitudinally aligned with the lumen and showed more intense staining with the anti-actin antibody. Myofibroblasts closest to the media were stellate in appearance, randomly aligned, and stained weakly for alpha-actin.

Figure 3:
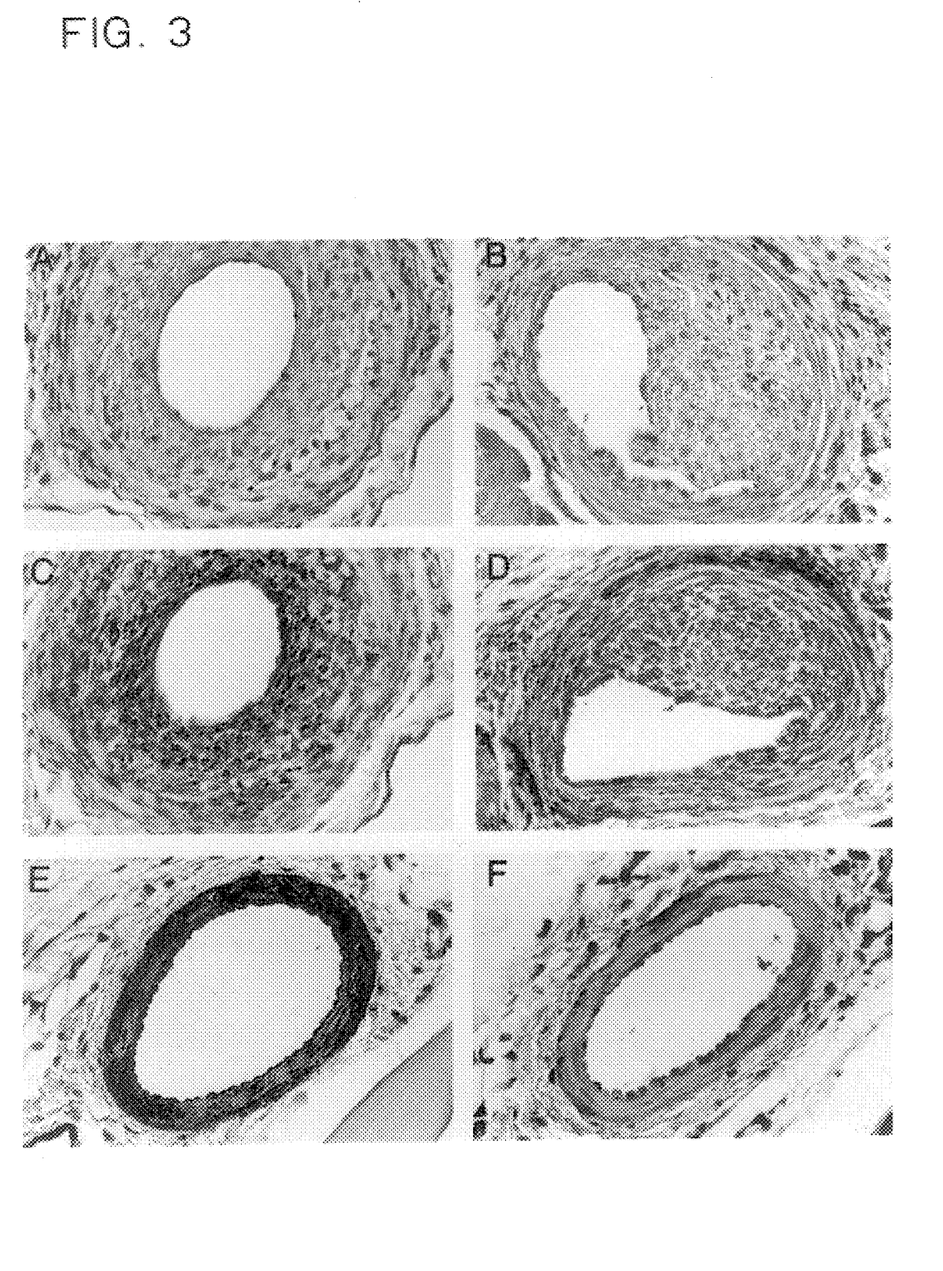
FIGS. 3A–3F are photographs of stained artery tissue sections showing amplified EGF-receptor expression in neointimal hyperplasia.

The results are shown in FIG. 3. FIGS. 3A–3F are photographs showing amplified EGF-receptor expression in neointimal hyperplasia The neointima mass was stained positively with a monoclonal anti-alpha-actin antibody (FIG. 3C) and with a rabbit polyclonal anti-EGF receptor antibody (FIG. 3D) and stained negatively with the control mouse antibody (FIG. 3A) and the rabbit antibody (FIG. 3B). The uninjured right femoral artery was strongly stained with anti-actin antibody (FIG. 3E) and weakly stained with anti-EGF receptor antibody (FIG. 3F).

The cellular elements of the hyperplastic neointima are α-actin positive vascular smooth muscle cells expressing epidermal growth factor receptor at high levels. Notably, the neointima of the injured femoral artery stained more intensely with anti-EGF-receptor antibody than the media, as well as the intima of the uninjured femoral arteries. These findings indicate that the EGF receptor function and EGF receptor linked signal transduction events may be essential for the migration and proliferation of myofibroblasts contributing to the neointimal hyperplasia formation after vascular injury.

Example 4

EGF-Genistein Prevents Restenosis

Vascular injury was induced in C57B1/6 mice as described for Example 2. Following irradiation, the mice were treated for either 14 days or 28 days with intraperitoneal injections of (1) EGF-Gen or unconjugated EGF (modified EGF not conjugated to genistein) at a dose level of 0.1 mg/kg/dose, once in the morning and once in the evening. For 14 day treatment, this dose represents a cumulative total dose level of 2.8 mg/kg and 2% of the highest nontoxic cumulative dosed tested in toxicity studies (Uckun et al., 1998, *Clinical Cancer Res* 5:1125–1134). For 28 day treatment, this dose represents a cumulative total dose level of 5.6 mg/kg and 4% of the highest nontoxic cumulative dosed tested in toxicity studies. Control animals were injected with 2 mg/kg/dose of unconjugated genistein or derivatives of 6, 7-dimethoxyquinizalone dissolved in 10% DMSO once per day or with PBS.

At the times indicated, the animals were sacrificed and perfused with PBS followed by 4% phosphate buffered formalin. Serial sections were made and stained for histopathological studies. Sections stained for histopathological studies were stained with hematoxylin and eosin or Masson's trichrome.

At the end of the treatment period, mice were euthanized and tissue sections containing the femoral artery were embedded and serially sectioned. Neointima/media ratios in areas of maximum neointimal hyperplasia were determined by histomorphometric analysis. Control mice were treated with EGF, Gen, or quinazoline derivatives, as described above.

As shown in Table 2, neointima was detected in all of the 24 EGF-Gen conjugate treated mice at 4 weeks post injury. However, the mean neointima/media ratio (stenosis index) in areas of maximum neointimal hyperplasia was 0.59±0.16 which was significantly lower than the stenosis index values for control mice treated with PBS, genistein, or quinazoline derivatives (P values by two-tailed Mann-Whitney t-test: EGF-Gen vs. PBS =0.002, EGF-Gen vs. genistein=0.009, and EGF-Gen vs. quinazolines=0.002.).

Figure 4:
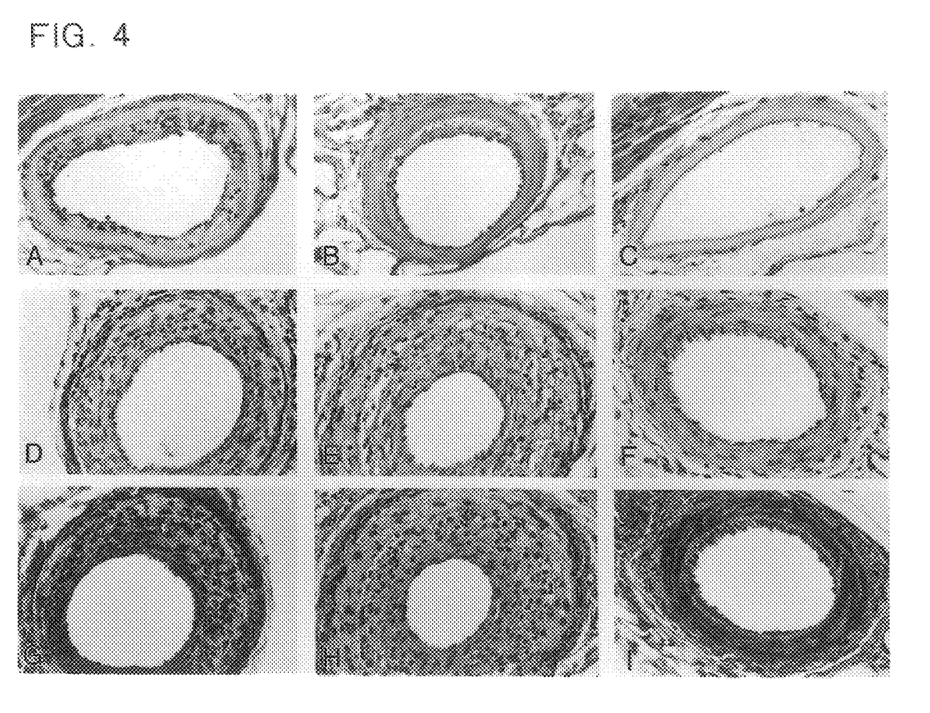
FIGS. 4A–4I are photographs of stained artery tissue sections showing inhibition of neointimal hyperplasia in tissues treated with EGF-Genistein.
Figure 5:
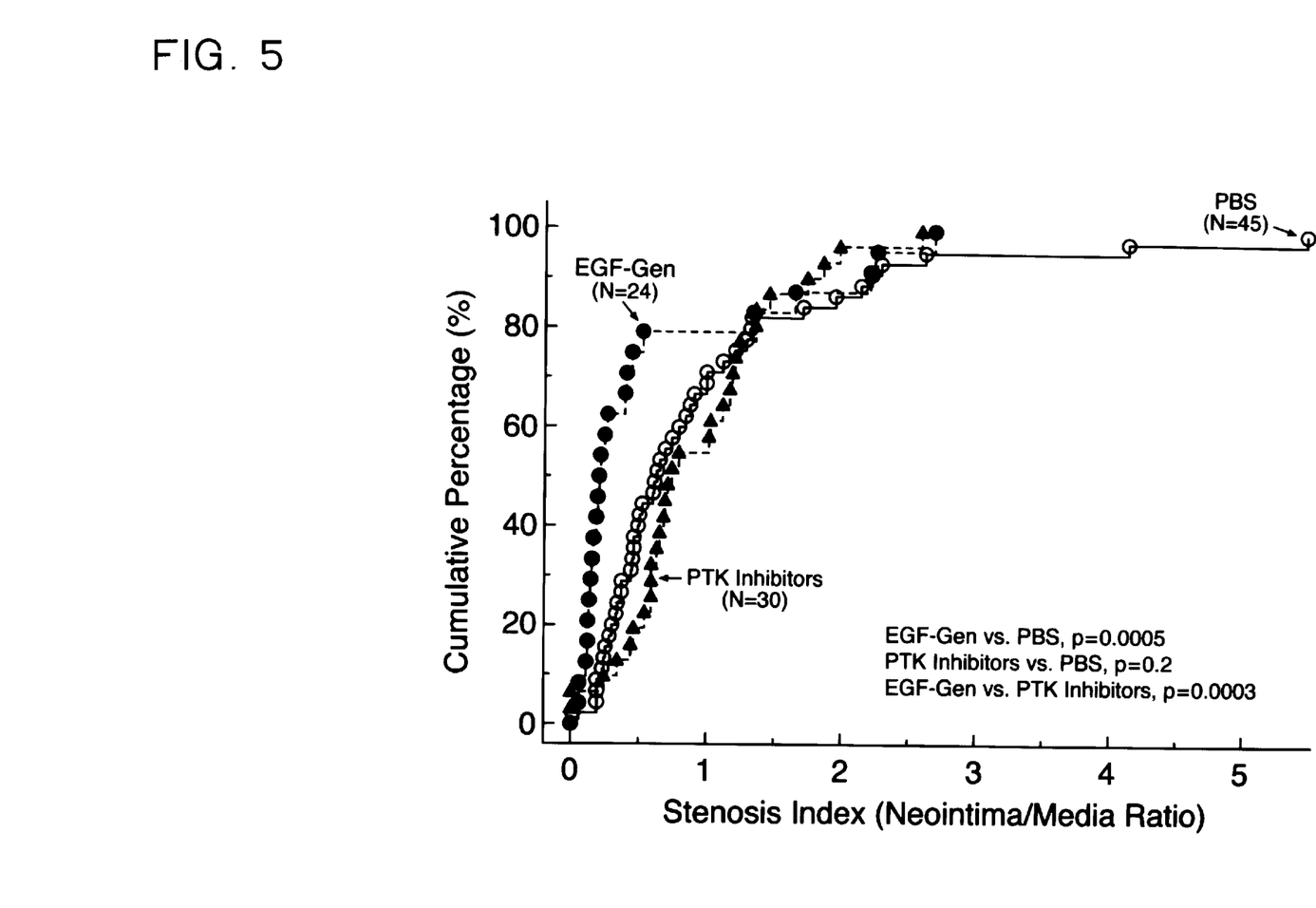
FIG. 5 is a graph demonstrating prevention of neointima formation in artery tissues treated with EGF-Genistein.

The results are shown in Table 2, FIG. 4, and FIG. 5. Neointima/media ratios and areas of maximum neointimal hyperplasia were determined by histomorphometric analysis.

At two weeks after vascular injury, neointimal hyperplasia was detected in 13 of 15 (87%) PBS-treated control mice and 6 of 8 (75%) mice treated with unconjugated EGF. Morphometric analysis of serial tissue sections using the NIH image 1.61 program revealed no differences between these two groups of mice (mean neointima/media ratios: 0.73±0.13 versus 0.63±0.20, p=0.7). In contrast, none of the 5 mice treated with EGF-Gen for two weeks showed neointimal hyperplasia (P=0.00 1 for EGF-Gen vs. PBS; P=0.02 for EGF-Gen vs. unconjugated EGF, Fisher's exact test) and their mean neointima/media ratio (=stenosis index) was 0.0±0.0 (Table 2, FIG. 3).

TABLE 2

Effect of EGF-Gen on Vascular Injury-Induced Neointimal Hyperplasia. Stenosis Index (Mean ± SE)

| Treatment | 2 weeks | 4 weeks |
| --- | --- | --- |
| PBS | | 0.99 ± 0.16 (N = 45) |
| EGF-Gen | 0.00 ± 0.00 (N = 5) | 0.59 ± 0.16 (N = 24) |
| EGF | 0.63 ± 0.20 (N = 8) | N.D. |
| Gen | N.D. | 1.03 ± 0.18 (N = 8) |
| Quinazolines | N.D. | 0.94 ± 0.13 (N = 22) |

The treatment inhibited the migration of myofibroblasts into the damaged vascular wall and formation of neointima. At two weeks after vascular injury, neointimal hyperplasia was detected in 13 of 15 (87%) PBS treated control mice and 6 of 8 (75%) treated with unconjugated EGF. Morphometric analysis of serial tissue sections using NIH image 1.61 program revealed no differences between these two groups of mice. In contrast, none of the five mice treated with EGF-Gen for two weeks showed neointimal hyperplasia and their mean neointima/media ratio (stenosis index) was 0.0±0.0.(P=0.001 for EGF-Gen vs. PBS; P=0.02 for EGF-Gen vs. unconjugated EGF, Fisher's exact test).

At four weeks after vascular injury, serial tissue sections from PBS treated control mice and mice treated with EGF-Gen for a total of four weeks were subjected to histomorphometric analysis to determine the effects of EGF-Gen on development and magnitude of neointimal hyperplasia. As discussed previously, EGF-Gen significantly reduced the magnitude of neointimal hyperplasia in injured femoral arteries. Unlike EGF-Gen, 3 quinazoline based EGF receptor tyrosine kinase inhibitors failed to suppress the development of neointimal hyperplasia in injured femoral arteries (stenosis index=0.94±0.13, n=22; EGF-Gen vs. quinazoline derivatives, P=0.002).

The distribution pattern of the cumulative percentage vs. stenosis index plot for EGF-Gen (n=24) was significantly different from that for PBS (n=45) or other PTK inhibitors (n=30 including Gen, n=8, and 3 different quinazoline derivatives, n=22) (P-values by Wilcoxon statistics: EGF-Gen vs. PBS, P=0.0005; EGF-Gen vs. other PTK inhibitors, P=0.0003).

The mean neointima/media ratios for areas of maximum neointimal hyperplasia were 0.59±0.16 (n=24) for the EGF-Gen treated group, 0.99±0.16 (n=45) for the PBS group (EGF-Gen vs. PBS, p=0.002, two tailed Mann-Whitney t-test) and 1.03±0.18 (n=8) for the control group treated with unconjugated Gen (EGF-Gen vs. Gen, p-0.009, two tailed Mann-Whitney t-test). Unlike EGF-Gen, three quinazoline-based EGF-receptor tyrosine kinase inhibitors failed to suppress the development of neointimal hyperplasia in injured femoral arteries, 0.94±0.13 (n=22) (EGF-Gen vs. Quinazoline derivatives, p=0.002, two-tailed Mann-Whitney t-test).

These results show that at a dose level of less than 5% of the highest nontoxic dose, EGF-Genistein suppressed migration of myofibroblasts into the mural thrombus and the formation of neointima. The pronounced inhibition of the neointiamal hyperplasia seen with EGF-Genistein treatment indicates that this biotherapeutic agent is useful as a non-toxic prophylactic drug for the prevention of restenosis. Unconjugated EGF or genistein were ineffective in inhibiting or preventing neointimal hyperplasia Example 5

Expression of EGF-R on VSMC

Figure 6A:
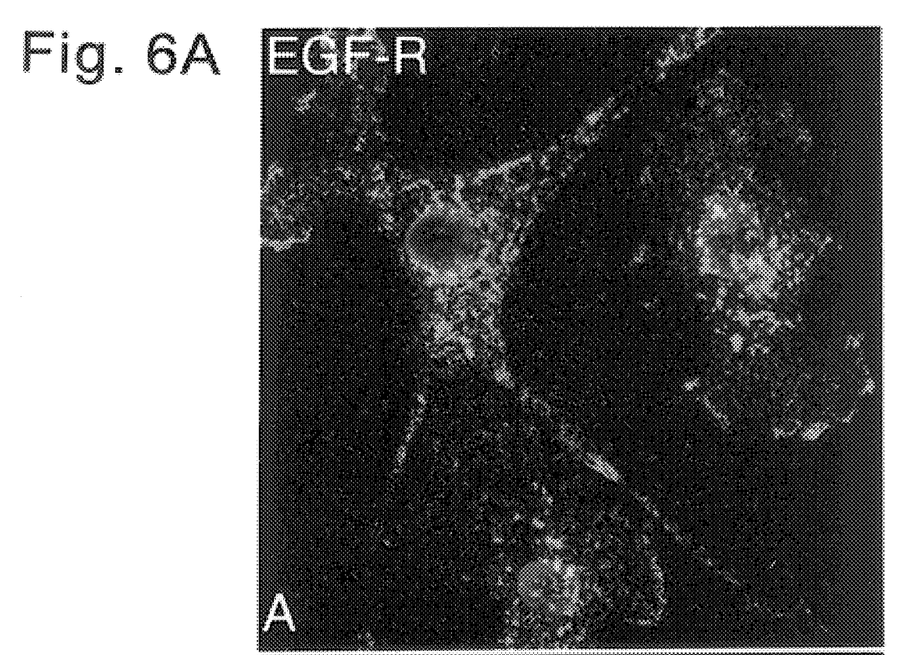
FIG. 6A is a photograph of confocal laser microscopy of vascular smooth muscle cells stained with anti-EGFR antibody (green flourescense).
Figure 6B:
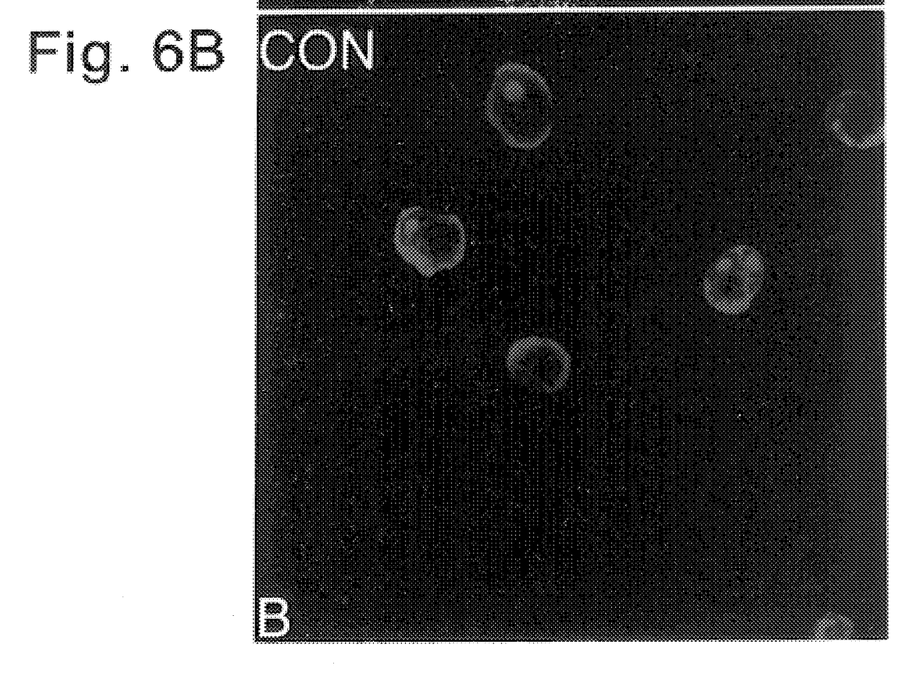
FIG. 6B shows the control analysis in the absence of the anti-EGFR antibody.

The expression of EGF Receptor on vascular smooth muscle cells (VSMC) was analyzed using the methods described above for Example 4. VSMC were stained with monoclonal antibody against EGF-R and analized by confocal laser scanning microscopy Membrane-associated bright green fluorescence was consistent with surface expression of EGF Receptors (FIG. 6A and 6B). Cells were fixed in 2% paraformaldehyde and immunostained with monoclonal antibody against EGF-R (FIG. 6A, green fluorescence). These results are in accordance with a recent report of high level EGF-R expression in proliferating vascular smooth muscle cells (Saltis et al., 1995, *Atherosclerosis* 118: 77–87). Red fluorescence represents nuclei stained with PI. Controls in which primary antibody was omitted showed no green fluorescence (FIG. 6B).

Example 6

EGF-Genistein Inhibits VSMC Migration

Migration of VSMC through Matrigel™ matrix was performed as described above for Example 4. As shown in FIGS. 7A–F, EGF-genistein inhibited the migration of VSMC in a dose dependent fashion, with complete cessation of in vitro migration at 1 μg/ml. In contrast, unconjugated EGF significantly promoted the migration of VSMC.

Figure 7A:
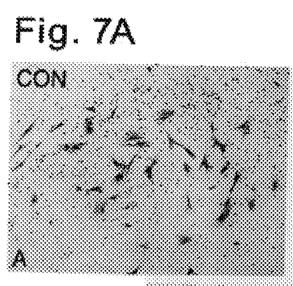
FIGS. 7A–7E show a panel of photographs showing the morphology of vascular smooth muscle cells migrated through Matrigel matrix. Control (FIG. 7A), and EGF-gen-treated (FIGS. 7B–E) cells are shown.
Figure 7B:
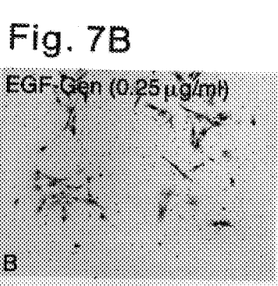
Figure 7C:
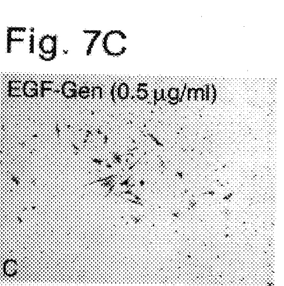
Figure 7D:
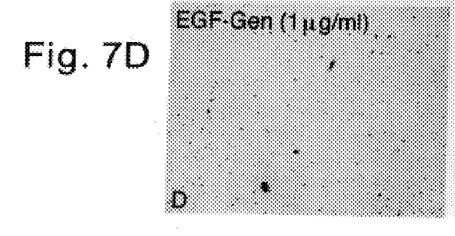
Figure 7E:
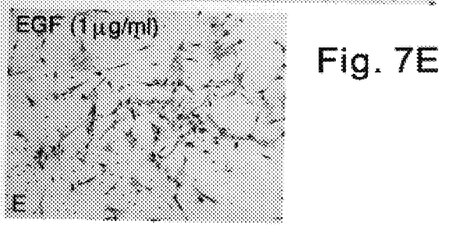
Figure 7F:
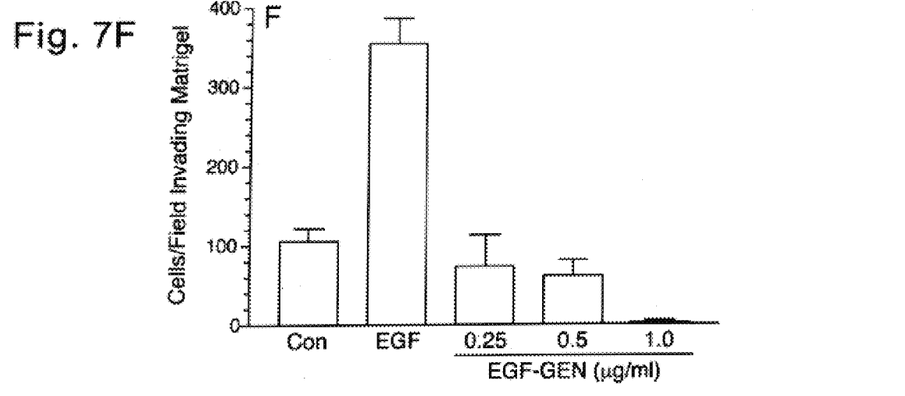
FIG. 7F is a graph quantitating data of the migrated cells.

FIGS. 7A–7E show the morphological features of migrated VSMC incubated with 0.25 μg/ml (FIG. 7B), 0.5 μg/ml (FIG. 7C), or 1 μg/ml (FIG. 7D) of EGF-gen or with 1 μg/ml EFG (FIG. 7E), overnight. The control (FIG. 7A) was untreated. The cells were then trypsinized and processed for the migration assay using Matrigel™ matrix-coated boyden chambers. Cells migrated through the matrigel and were counted and expressed as % of controls. FIG. 7F is a bar graph showing the dose dependent inhibition of migration by EGF-Gen.

The above specification includes reference to numerous publications, including patents and patent applications. Each such reference is hereby incorporated by reference for all purposes.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method for preventing or treating vascular restenosis comprising:
   administering an effective amount of conjugate protein comprising epidermal growth factor (EGF) and a tyrosine kinase inhibitor to an animal prior to, during, or after induction of vascular injury.

2. The method of claim 1, wherein the vascular injury is associated with an angioplasty procedure.

3. The method of claim 1, wherein the tyrosine kinase inhibitor is a flavinoid, a leflunomide, or a quinazoline tyrosine kinase inhibitor.

4. A method for preventing or treating vascular restenosis comprising:
   administering an effective amount of conjugate protein comprising epidermal growth factor (EGF) and a tyrosine kinase inhibitor to an animal prior to, during, or after induction of vascular injury, wherein the conjugate protein is EGF-genistein.

5. The method of claim 1, wherein the animal is a human.

6. The method of claim 1, wherein the conjugate protein is administered locally through an implantable device.

7. The method of claim 1, wherein said administering comprises administering the conjugate protein prior to induction of vascular injury.

8. The method of claim 1, wherein the conjugate protein is administered before and after induction of vascular injury.

9. A method for preventing or treating vascular restenosis comprising:
   administering an effective amount of conjugate protein comprising epidermal growth factor (EGF) and a tyrosine kinase inhibitor to an animal prior to, during, or after induction of vascular injury,
   wherein the conjugate protein is EGF-genistein; and wherein the EGF-genistein is administered at least two days before induction of vascular injury.

10. The method of claim 3, where the tyrosine kinase inhibitor is a flavinoid.

11. The method of claim 3, where the tyrosine kinase inhibitor is an isoflavone.

12. The method of claim 3, where the tyrosine kinase inhibitor is genistein, diadzein, or biochannin A.

13. The method of claim 3, where the tyrosine kinase inhibitor is a quinazoline.

14. The method of claim 1, wherein an amount of said tyrosine kinase inhibitor is administered to yield a systemic exposure of about 0.28 μg/liter/hour or greater.

15. The method of claim 1, wherein said tyrosine kinase inhibitor is administered at a dose of at least 25 μg/kg body weight.

16. The method of claim 15, wherein said dose is about 1 to about 5 mg/kg body weight.

17. The method of claim 2, wherein said administering is about 1 to 3 days prior to angioplasty procedure.

18. The method of claim 2, wherein said administering is during angioplasty procedure.

19. The method of claim 18, wherein said administering is both prior to and during angioplasty procedure.

* * * * *